United States Patent [19]

Anbergen

[11] 4,144,531

[45] Mar. 13, 1979

[54] DROWSINESS DETECTING APPARATUS

[76] Inventor: Henricus J. Anbergen, 9, rue des Espagnols, Arlon, Belgium

[21] Appl. No.: 841,417

[22] Filed: Oct. 12, 1977

[30] Foreign Application Priority Data

Oct. 12, 1976 [LU] Luxembourg .............................. 75977

[51] Int. Cl.² ............................................. G08B 21/00
[52] U.S. Cl. .................................. 340/575; 340/526; 340/576; 315/129
[58] Field of Search ................... 340/213 R, 275, 279, 340/52 D, 500, 501, 573, 575, 576, 526; 315/129, 132, 287

[56] References Cited

U.S. PATENT DOCUMENTS 2,726,380  12/1955  Campisi .................................. 340/279

*Primary Examiner*—Alvin H. Waring
*Attorney, Agent, or Firm*—Sughrue, Rothwell, Mion, Zinn and Macpeak

[57] ABSTRACT

A safety apparatus for detecting an individual becoming drowsy is provided comprising a wave emitter mounted on an eyeglasslike frame for emitting a wave along a path directed to pass close to the individual's eyeball without impinging the latter such that said wave is interrupted by the eyelashes when the eyelid is quivering, and detecting means on the frame for generating a signal in response to the wave being interrupted. Signalling means is provided to produce an alarm signal a predetermined time after the last eyelid quivering.

2 Claims, 3 Drawing Figures

U.S. Patent  Mar. 13, 1979  Sheet 1 of 2  4,144,531
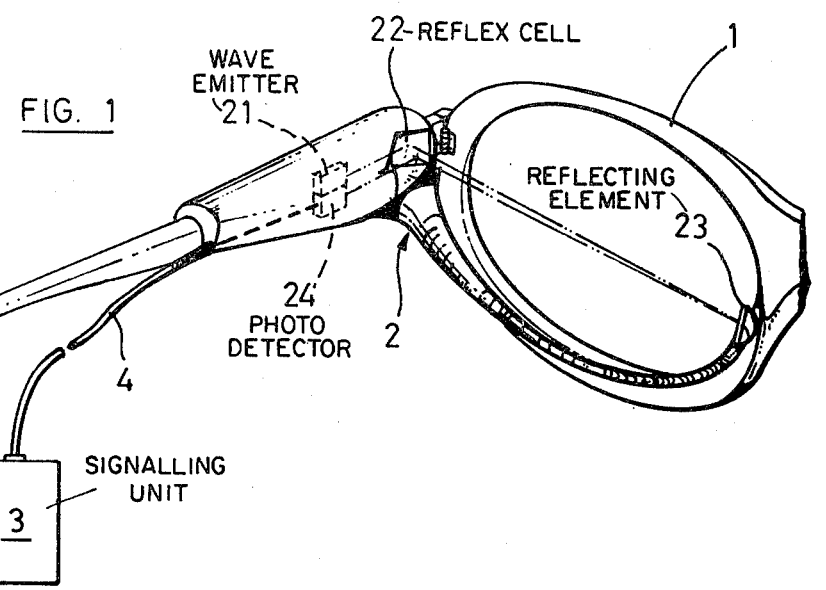
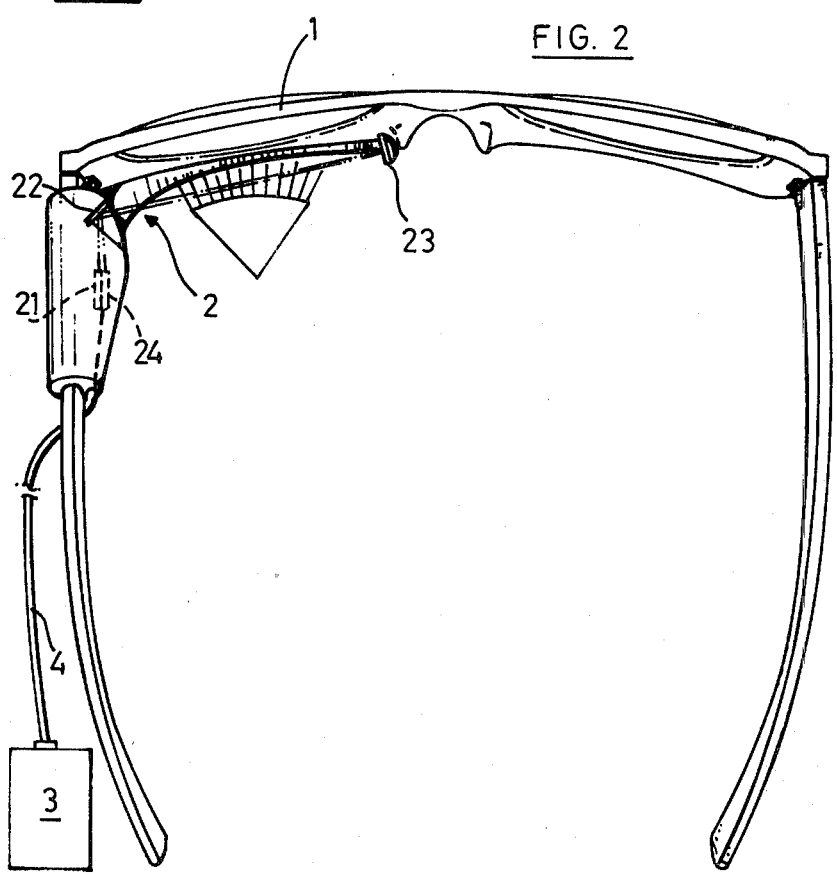

DROWSINESS DETECTING APPARATUS

The present invention relates to a safety apparatus for detecting an individual becoming drowsy.

The usefulness and even the need for a safety apparatus to be used to arouse an individual who is becoming drowsy at the controls of a machine or a vehicle for instance is obvious.

A known apparatus (French Pat. No. 1.591.458) uses the reflection of a wave beam onto the surface of the individual's eye, the reflected beam impinging a detector adapted to actuate an alarm device when the intensity of the reflected beam decreases substantially during a predetermined time, that is when the eyelid remains closed during a predetermined time. The drawback of this known apparatus however is that, when used by a vehicle operator for instance, it can cause the alarm device to be actuated when the operator is dazzled by the headlights of a vehicle running in opposite direction or by the road lighting. Furthermore, this known apparatus appears to be disturbing and inconvenient or even to be harmful at the physiological point of view as far as the eyeball is continuously irradiated by the wave beam.

The object of the invention has been to provide a safety apparatus which is effective and safe and which causes not any inconvenience.

According to the invention, a safety apparatus is provided comprising a frame similar to an eyeglass frame, wave emitter means mounted on the frame for emitting a wave along a path directed to pass close to the individual's eyeball without impinging the latter when the frame is carried on the nose of the individual like an eyeglass frame such that said wave is interrupted by the eyelashes when the eyelid is quivering, and detector means mounted on the frame for being impinged by said wave and for generating a signal in response to said wave being interrupted.

In a particular embodiment this apparatus further comprises signal generator means for generating a control signal, counter means connected to be advanced by said control signal and to be reset in response to each signal from said detector means, this counter means being further connected for generating a warning signal in response to reaching a predetermined count, and alarm means connected to be actuated by said warning signal from the counter.

The drawings herein depict a preferred embodiment:

FIG. 1 is a partial perspective view of a frame with the wave emitter and detector means;

FIG. 2 is a top view of the frame shown partially in FIG. 1;

Figure 3:
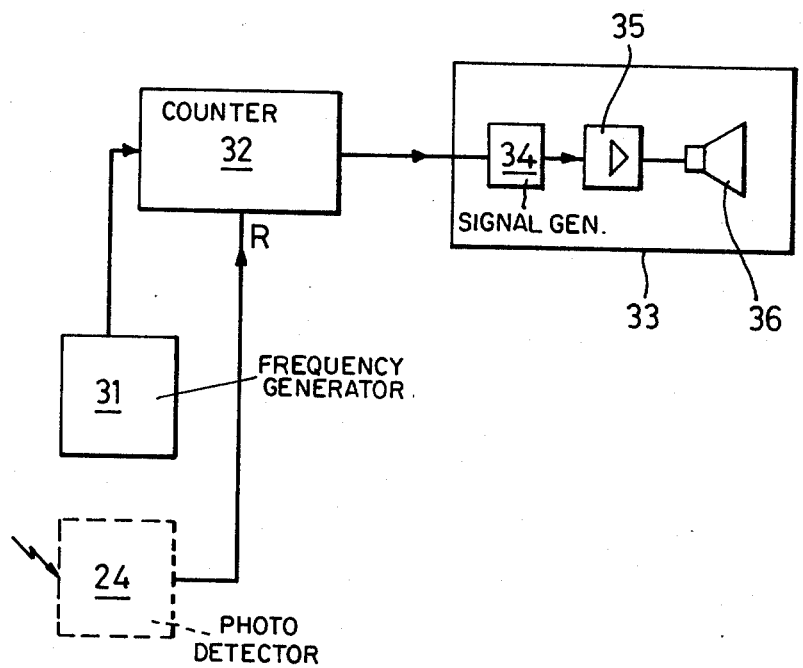
FIG. 3 is a schematic diagram of the signalling unit.

As shown in FIGS. 1 and 2, the apparatus according to the invention comprises two units: a photodetector unit 2 mounted on a frame 1 similar to an eyeglass frame and a signalling unit 3. The photodetector unit 2 can be formed solid with the frame 1 or it can be made to be attached to a separate frame. The photodetector unit 2 essentially comprises a wave emitter 21 and a photodetector 24. The wave emitter 21 is adapted to emit an electromagnetic or infrared wave along a path directed to pass close to the individual's eyeball without impinging the latter when the frame is carried on the nose of an individual, such that said wave is interrupted by the eyelashes when the eyelid is quivering. In the preferred embodiment shown in FIGS. 1 and 2 the wave from the emitter 21 is directed to a reflex cell 22 which reflects the wave toward a reflecting element 23 also mounted on the frame 1 for reflecting the wave back to the reflex cell 22 and then toward the detector 24. The latter is adapted to generate a signal in response to the wave being interrupted. This detector signal is coupled to the signalling unit 3 by wire 4 as shown in the drawings or wireless.

The signalling unit 3 is a separate unit comprising electronic circuitry for processing the detector signal and producing an alarm signal. FIG. 3 is a schematic diagram of this electronic circuitry. A frequency generator 31 generates an uninterrupted control signal for advancing a counter 32. The latter is connected to be reset by the signal from the detector 24 in the photodetector unit 2 and to produce a warning signal when reaching a predetermined count. The frequency generator 31 is advantageously a low frequency generator for generating a frequency which can be adjusted in the range of 4 Hz to 0.8 Hz; in that case the counter 32 can be adapted for instance to produce a warning signal after a time delay between 4 and 20 seconds.

The warning signal from counter 32 is applied to an alarm device 33. The latter may comprise a signal generator 34 producing an audio signal for actuating a loudspeaker 36 through a power amplifier 35. Obviously, use can be made of the loudspeaker of a vehicle radio set.

What is claimed is:

1. A safety apparatus for detecting an individual becoming drowsy comprising:
   (a) a frame similar to an eyeglass frame;
   (b) wave emitter means mounted on the frame for emitting a wave along a path directed to pass close to the individual's eyeball without impinging the latter when the frame is carried on the nose of the individual like an eyeglass frame such that said wave is interrupted by the eyelashes when the eyelid is quivering;
   (c) detector means mounted on the frame for being impinged by said wave and for generating a signal in response to said wave being interrupted;
   (d) frequency generator means for generating a control signal;
   (e) counter means connected to be advanced by said control signal and to be reset in response to each signal from said detector means, said counter means being further connected for generating a warning signal in response to reaching a predetermined count; and
   (f) alarm means connected to be actuated by said warning signal from the counter.

2. An apparatus according to claim 1, further comprising:
   (a) reflex cell means mounted on said frame for reflecting the wave from said emitter means;
   (b) reflecting means mounted on said frame for reflecting the wave from said reflex cell means back to said reflex cell means along a path passing close to the individual's eyeball such that said wave is interrupted by the eyelashes when the eyelid is quivering.

* * * * *